United States Patent

Gronka

(12) United States Patent
(10) Patent No.: US 6,725,568 B2
(45) Date of Patent: Apr. 27, 2004

(54) EAR CANAL DRYER AND METHOD OF USE THEREOF

(76) Inventor: Edward A. Gronka, 39 Tilbury Ave., W. Nanticoke, PA (US) 18634-0115

( * ) Notice: Subject to any disclaimer, the term of this patent is extended or adjusted under 35 U.S.C. 154(b) by 0 days.

(21) Appl. No.: 10/367,904

(22) Filed: Feb. 19, 2003

(65) Prior Publication Data

US 2004/0060192 A1 Apr. 1, 2004

Related U.S. Application Data

(60) Provisional application No. 60/414,663, filed on Oct. 1, 2002.

(51) Int. Cl.$^7$ .............. F26B 7/00; A61B 1/04; A61M 31/00; A61F 11/00
(52) U.S. Cl. .............. 34/437; 34/487; 34/69; 34/90; 34/104; 600/114; 604/48; 604/500; 606/109; 606/162
(58) Field of Search .......... 34/398, 402, 443, 34/487, 218, 230, 232, 241; 606/109; 604/19, 26, 37, 45, 264, 319

(56) References Cited

U.S. PATENT DOCUMENTS

| | | | |
|---|---|---|---|
| 4,380,998 A | * 4/1983 | Kieffer et al. | 600/200 |
| 5,297,477 A | * 3/1994 | Phillips | 99/495 |
| 5,312,331 A | * 5/1994 | Knoepfler | 604/500 |
| 5,665,094 A | * 9/1997 | Goldenberg | 606/109 |
| 5,787,799 A | * 8/1998 | Mohrhauser et al. | 99/345 |
| 5,979,072 A | * 11/1999 | Collins, II | 34/90 |
| 6,059,803 A | * 5/2000 | Spilman | 606/162 |
| 6,086,516 A | * 7/2000 | Santos | 482/5 |
| 6,258,024 B1 | * 7/2001 | van Der Weegen | 600/115 |
| 6,290,667 B1 | * 9/2001 | Cook | 604/19 |
| 6,390,975 B1 | * 5/2002 | Walls et al. | 600/200 |
| 6,458,094 B1 | * 10/2002 | McMahon et al. | 604/35 |
| 6,599,297 B1 | * 7/2003 | Carlsson et al. | 606/109 |

* cited by examiner

*Primary Examiner*—Pamela A Wilson
(74) *Attorney, Agent, or Firm*—Raymond VanDyke; Nixon Peabody, LLP

(57) ABSTRACT

An ear canal dryer that removes excess fluid or moisture retained in the outer ear canal. The ear canal dryer comprises a bulb and a speculum, each having an air flow controller. By inserting the speculum into the ear canal and squeezing the bulb, an air stream is injected into the ear canal causing evaporation of fluid and carrying the moisture out of the canal. The ear canal dryer of the present invention is easy to carry and use. It can be manufactured at a low cost and may also be adapted for veterinary use.

12 Claims, 2 Drawing Sheets

VIEW I-II

EAR CANAL DRYER AND METHOD OF USE THEREOF

RELATED APPLICATION

This application claims the benefit of U.S. Provisional Application Serial No. 60/414,663, filed Oct. 1, 2002.

TECHNICAL FIELD

The technical field relates to medical devices in general, and in particular to a device for removing excess moisture retained in the outer ear canal.

BACKGROUND

The ear is a complex structure that consists of three sections: the outer, middle, and inner ears. The outer ear (also called outer ear canal) is the short passage from the outside of the ear to the ear drum, which is an inch or so inside the ear of human beings. Infection of the outer ear (infective otitis externa) is quite common. The infection causes swelling, redness, heat and pain, and is often associated with temporary deafness as swelling and discharge may block the ear canal. The infection-related swelling may also affect the ear drum itself.

Infective otitis externa is usually caused by a bacteria or fungus infection of the outer ear canal. The infection can happen to anyone. One of the most common causes is swimming in bacteria-infected waters. Another common cause is excess moisture in the outer ear canal, which creates a moist environment that bacteria and fungi find most attractive for growth. The excess moisture in the outer ear canal may be generated by water retention in the ear after a shower or swimming, by wearing a hearing aid that blocks air circulation in the outer ear for an extended period of time, or by certain ear diseases such as mastoid cavities, tympanic membrane perforations and abnormal ear canal structures with reduced ear canal openings.

The commonly recommended method for removing excess moisture retained in the outer ear canal is to use a hair dryer to blow air into the ear. It has been suggested to aim a hair dryer to the ear from 18 to 20 inches away, using either a warm or cool setting. However, it was difficult to force air into a small closed-end opening such as the ear canal even with a hair dryer. In fact, the air flow created by the hair dryer held at a distance from the ear actually compresses the existing air in the ear canal and does not provide the requisite air circulation needed to dry the moisture.

U.S. Pat. No. 5,979,072 to Collins et al. generally describes an external ear canal drying apparatus that is capable of blowing heated air into the ear canal through an adaptor that fits the opening of outer ear. The electrical-powered, motorized device, however, is complicated and expensive to manufacture. In addition, its pistol shaped configuration would make it questionable for air travel by users. There still exists the need for a simple, inexpensive and easy-to-use device that can efficiently and safely remove moisture from outer ear canal.

SUMMARY

The present invention is directed to an ear canal dryer that removes excess fluid or moisture retained in the outer ear canal. The ear canal dryer of the present invention includes a bulb and a speculum, each having an air flow controller. By inserting the speculum into the ear canal and squeezing the bulb, an air stream is injected into the ear canal causing evaporation of fluid and carrying the moisture out of the canal through escape vents along the outer surface of the speculum. The air flow controllers in the bulb and speculum serve two major functions: (1) directing the air stream into the ear canal and (2) preventing the moisture-laden air expelled from the ear canal to re-enter the bulb. The ear canal dryer of the present invention is easy to carry and use. It can be manufactured at a low cost and may also be adapted for veterinary use.

Presently preferred embodiments of the inventions are described below in the Detailed Description of the Invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase.

It is further intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

For example, the disclosed device and method make use of ball-check valves to control air flow in and out of the bulb. Other air flow control mechanisms, such as manually activated external air check valves such used in conjunction with a bulb in a sphygmometer, could likewise be used. Thus, ball-check valves are shown and referenced generally throughout this disclosure, and unless specifically noted, are intended to represent any and all air flow control mechanisms appropriate to utilize the principles taught herein.

Likewise, there is disclosed a grooved speculum that directs the air flow into the ear canal. The specific shape and form of the grooved speculum can vary. It will be realized by those of ordinary skill in the art that the invention can be implemented using grooved speculums of various shapes as long as they may effectively direct the air flow to the outer ear canal and facilitate the air exchange in the ear. Thus, it is not Applicant's intention to limit his invention to any particular form of grooved speculum.

Further examples exist throughout the disclosure, and it is not Applicants intention to exclude from the scope of his invention the use of structures, materials, or acts that are not expressly identified in the specification, but nonetheless are capable of performing a claimed function.

BRIEF DESCRIPTION OF THE DRAWINGS

The detailed description will refer to the following drawings, in which like numerals refer to like elements, and in which.

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the spirit and scope of the invention. The present invention is not intended to be limited to the embodiments shown, but is to be accorded the widest possible scope consistent with the principles and features disclosed herein.

Figure 1:
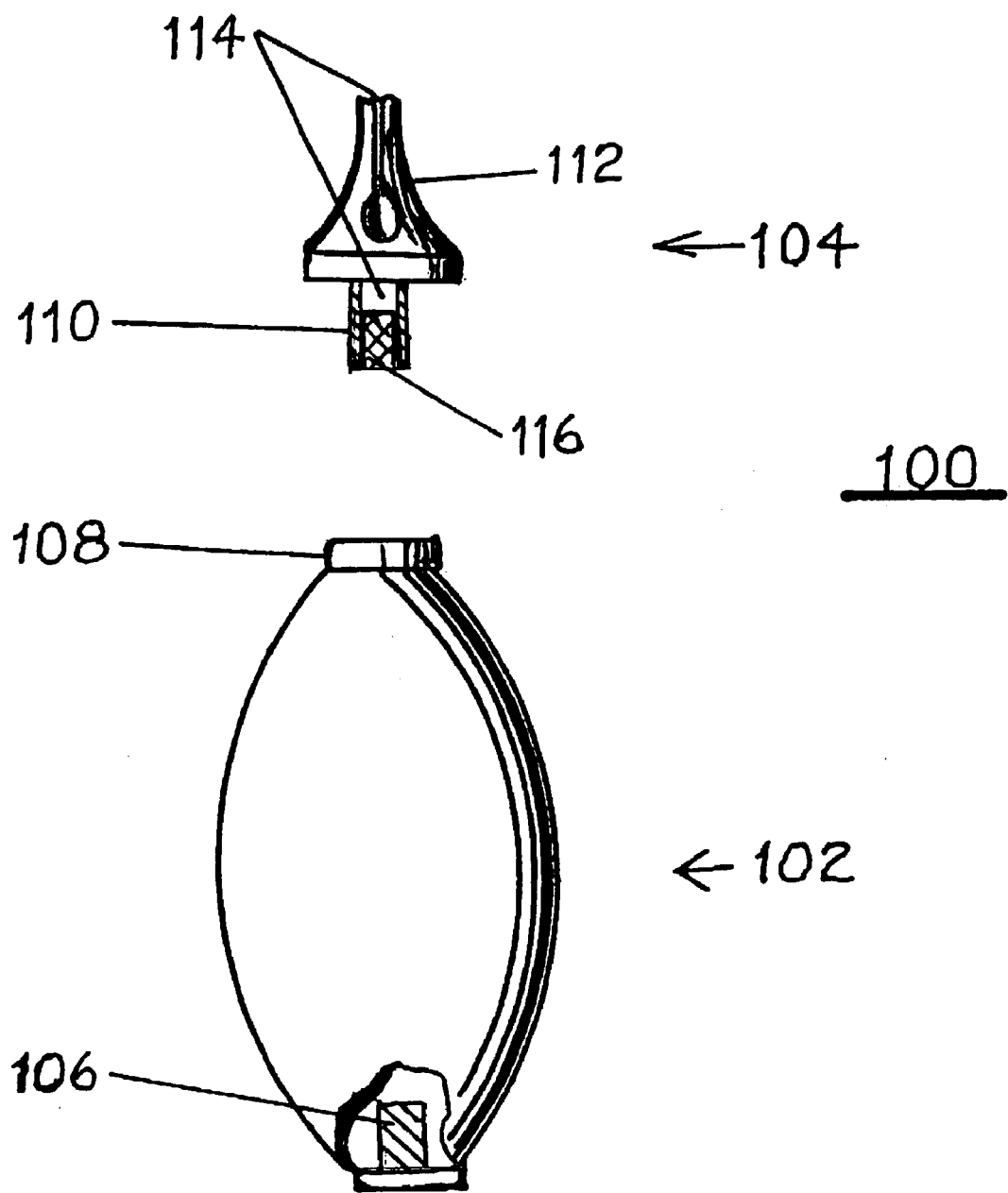
FIG. 1 illustrates an embodiment of an ear canal dryer in accordance with the principles of the present invention.

FIG. 1 depicts an embodiment of an ear canal dryer, generally designated by the reference numeral 100, utilizing the principles of the present invention. The ear canal dryer 100 includes an elastic bulb and a speculum, generally designated by the reference numerals 102 and 104, respectively. The elastic bulb 102 contains an air intake controller 106, as shown in the cut-out view, and an air exhaust port 108. It is well understood to one skilled in the art that the elastic bulb 102 can be of various sizes and can be made of any elastic material. In a preferred embodiment, the elastic bulb 102 is an approximately two ounce plastic/rubber bulb commonly used in medical devices, such as a sphygmometer. The air exhaust port 108 is so shaped to be connected to the speculum 104, which comprises a base 110 and a tapered head 112, as shown in the upper portion of FIG. 1.

Referring now to the speculum 104, an air passageway 114 within the base 110 and the tapered head 112 allows the air in the bulb 102 to exit the bulb through the tip of the tapered head 112 when the bulb 102 is squeezed. An air flow controller 116 inside the base 110 blocks the moisture-containing air in the ear canal from returning to the bulb 102 and allows fresh air to enter the bulb 102 through the air intake controller 106 for continued application. The head 112 may have external air flow directors to provide exit routes for air in the ear canal. In a preferred embodiment, the air intake controller 106 and air flow controller 116 are valves, and most preferably ball-check valves.

Figure 2A:
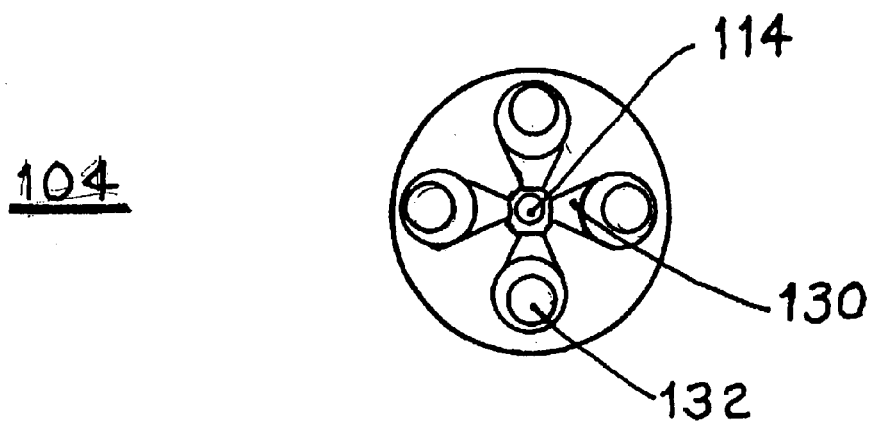
FIGS. 2A, 2B and 2C illustrate top, side, and sectional views, respectively, of a grooved speculum.
Figure 2B:
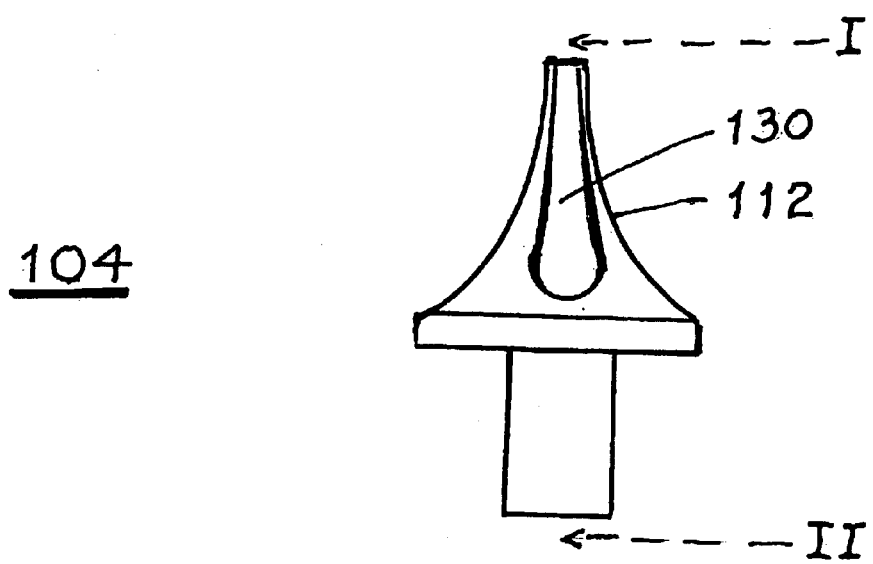
Figure 2C:
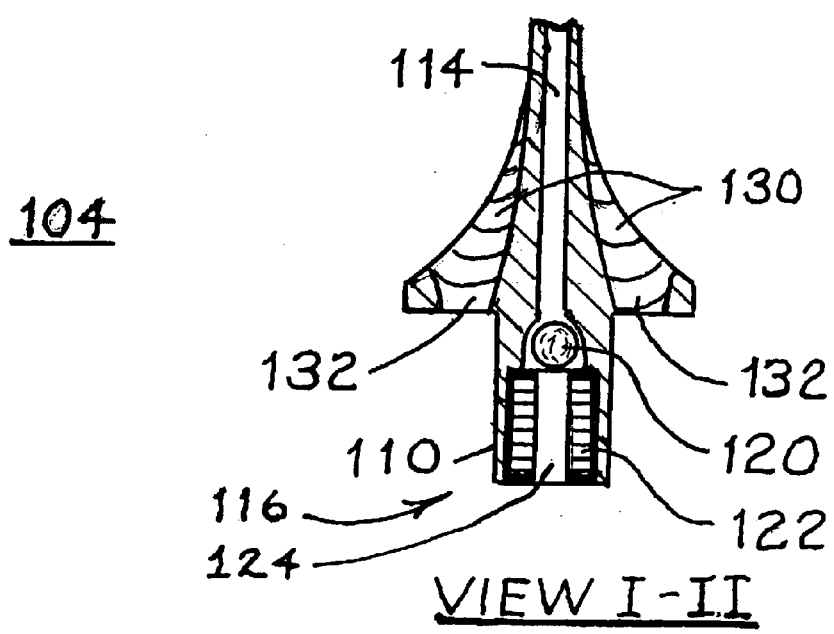

With reference now to FIGS. 2A, 2B and 2C, an embodiment of the speculum 104 is illustrated in more detail. In this embodiment, the exterior of the head 112 of the speculum 104 has multiple external air flow directors in the shape of grooves 130. Each groove 130 starts as a narrow trough at the tip of the head 112, then extends and expands to the other end of the head 112. As shown in FIGS. 2A and 2C, the groove 130 may have through-holes 132 at the expanded end to facilitate air release from the ear canal. As will be realized by one skilled in the art, the number and shape of the groove 130 is not critical to the invention, so long as the air inside the ear canal can be released effectively through the groove 130. The speculum 104 of the present invention can be made of plastics, ceramics, metal, or any other solid material. The speculum 104 can be manufactured by any molding, casting, press-forming or any other suitable method known in the art. In one embodiment, the speculum 104 is manufactured by injection molding using a tooling die fabricated to the required specifications.

FIG. 2C, a cross sectional view (I–II) of FIG. 2B, depicts an embodiment of the air flow controller 116. The air flow controller 116 has a precision ball bearing 120 followed by a tubular soft rubber insert 122. The rubber insert 122 is sized for a snug fit to the air passageway 114 within the base 110, as is understood in the art. The rubber insert 122 also has a through-hole 124 sized to pass sufficient air and has a proper length to provide a seat for the ball bearing 120. When the bulb 102 is squeezed, the air in side the bulb 102 pushes the ball bearing 120 away from the insert 122 and forms an air stream that is directed to the ear canal by the air passageway 114 within the speculum 104. When the pressure on bulb 102 is released, the bulb 102 expands and creates a low pressure zone inside the bulb. The ball bearing 120 would then be pushed towards the rubber insert 122 and blocks the air passageway 114. The fresh air may only enter the bulb 102 through the air intake controller 106. Therefore, the assembly of the base 110, the rubber insert 122, and the precision ball bearing 120 forms a ball-check valve that prevents the moisture-laden air in the ear canal from returning to the bulb 102.

The ear canal dryer of the present invention is easy to use. A user may simply insert the tip of the speculum 104 into the ear opening and squeeze the bulb 102. The compression of the bulb 102 will cause a unidirectional air stream to penetrate the ear canal thereby forcing moisture-laden air in the canal to be ejected across the surface of the speculum. The air flow controller 116 inside the speculum 104 prevents the moisture-containing air from returning to the bulb, and the grooves 130 on the exterior of the speculum 104 would facilitate the release of the moisture-laden air from the through-holes 132.

In the embodiment wherein the bulb 102 is a standard two ounce bulb, the bulb would have a volume of 29.57 $cm^3$. Since the average volume of an adult ear canal is about 2 $cm^3$, every squeeze of the bulb 102 would produce a gentle flow of air equal to approximately fifteen air changes in the ear canal. The drying effect is very noticeable as the user can feel the air temperature inside ear canal changing form cool (indicating liquid evaporation) to warn (indicating no evaporation). The user can usually stop the drying process when no temperature change is felt (indicating that all liquid has evaporated). The drying process normally takes 5–20 bulb squeezes.

Swimmers can use the ear canal dryer of the present invention to blow out the water entrapped in the ear. When water is entrapped from swimming, the surface tension of the fluid in the ear makes it difficult to relieve the condition. The customary treatment is to lower the head to the side of the affected ear, and then proceed to hop on one leg and beat the side of the tilted head with the palm of one's hand until the surface tension is broken, thus freeing the flow of water out of the ear. The ear canal dryer will generally remove all water in the ear canal with one squeeze of the bulb.

The ear canal dryer of the present invention is very useful for hearing aid users. The wet ear problems in hearing aid users are exacerbated due to the device being inserted in the ear for long periods of time. The ear canal dryer of the present invention is easy to carry and may be used periodically to remove moisture in the ear of the hearing aid users.

The ear canal dryer of the present invention can also be used for pets that are afflicted with the same problems as human beings. For example, dogs with floppy ears that cover the ear opening all the time often develop wet-ear problem that can be prevented by applying the ear canal dryer of the present invention on a daily basis.

Having described the preferred embodiments of a novel device and method for removing moisture from outer ear canal (which are intended to be illustrative and not limiting), applicant notes that modifications and variations can be made by persons skilled in the art in light of the above teachings. Therefore, it is understood that changes may be made in the particular embodiments disclosed which are within the scope and spirit of what is described as defined by the appended claims.

What is claimed is:

1. An apparatus for removing moisture from a cavity, said apparatus comprising:

a bulb device having an atmospheric air intake conduit at a first end thereof and an air exhaust port at a second end thereof, said air intake conduit comprising a first control means for directing air into said bulb device and preventing air from flowing out said air intake conduit, and a speculum device having a tapered end for insertion into said cavity and a second end, said speculum device being attached at said second end thereof to said air exhaust port of said bulb device, said speculum device having a passageway therethrough directing air exiting said bulb device into said cavity, said tapered end of said speculum device comprising an external air flow controlling means for directing air inside said cavity out alone the outer surface of said speculum device, whereby moisture within said cavity is removed by evaporation process.

2. The apparatus of claim 1, wherein said second end of the bulb device is distal of said first end of the bulb device.

3. The apparatus of claim 1, wherein the speculum device further comprising a second control means in said passageway for directing air exiting said bulb device.

4. The apparatus of claim 3, wherein the first and second control means are ball-check valves.

5. The apparatus of claim 1, wherein said external air flow controlling means is a groove.

6. An apparatus for removing moisture from a cavity, said apparatus comprising:

a bulb device having an atmospheric air intake conduit at a first end thereof and an air exhaust port at a second end thereof, said air intake conduit comprising a first check device for directing air into said bulb device and preventing air from flowing out said air intake conduit, and a speculum device having a tapered end for insertion into said cavity and a second end, said speculum device being attached at said second end thereof to said air exhaust port of said bulb device, said speculum device having a passageway therethrough directing air exiting said bulb device into said cavity, said tapered end of said speculum device comprising an external air flow director for directing air inside said cavity out along the outer surface of said speculum device, whereby moisture within said cavity is removed by evaporation process.

7. The apparatus of claim 6, wherein said second end of the bulb device is distal of said first end of the bulb device.

8. The apparatus of claim 7, wherein the speculum device further comprises a second check device in said passageway for directing air exiting said bulb device.

9. The apparatus of claim 8, wherein the first and second check devices are ball-check valves.

10. The apparatus of claim 6, wherein said external air flow director comprises a plurality of grooves on the exterior of said tapered end of said speculum device.

11. A method for removing moisture from a cavity, said method comprising steps of:

placing a tapered end of a speculum device into said cavity, said speculum device being connected to a bulb device, said tapered end of said speculum device having an external air flow director for directing air inside said cavity out and along the outer surface of said speculum device; and compressing said bulb device, driving air from within said bulb device through an exhaust port thereof into a passageway through said speculum device into said cavity, and out along the outer surface speculum device, whereby moisture within said cavity is removed by evaporation process.

12. The method of claim 11, wherein said external air flow director comprises groves on the exterior of said tapered end of said speculum device, permitting the moisture within said cavity to escape.

* * * * *